United States Patent [19]

Paatz et al.

[11] Patent Number: 5,846,798
[45] Date of Patent: Dec. 8, 1998

[54] MULTI-ENZYME GRANULES

[75] Inventors: Kathleen Paatz; Wilfried Rähse, both of Düsseldorf, Germany; Werner Pichler, Kundl, Austria; Horst Upadek, Ratingen; Norbert Kühne, Haan, both of Germany

[73] Assignee: Henkel Kommanditgesellschaft auf Aktien, Duesseldorf, Germany

[21] Appl. No.: 605,102

[22] PCT Filed: Aug. 22, 1994

[86] PCT No.: PCT/EP94/02779

§ 371 Date: May 13, 1996

§ 102(e) Date: May 13, 1996

[87] PCT Pub. No.: WO95/06709

PCT Pub. Date: Mar. 9, 1995

[30] Foreign Application Priority Data

Sep. 1, 1993 [DE] Germany .......................... 43 29 463.4

[51] Int. Cl.$^6$ .......................... C12N 11/02; C12N 11/14; C12N 9/98; D06M 16/00

[52] U.S. Cl. .......................... 435/187; 435/176; 435/177; 435/262; 435/264

[58] Field of Search ...................... 435/187, 176, 435/177, 262, 264

[56] References Cited

U.S. PATENT DOCUMENTS

| | | | |
|---|---|---|---|
| 3,623,957 | 11/1971 | Feldman | 435/222 |
| 4,264,738 | 4/1981 | Stepanov et al. | 435/222 |

FOREIGN PATENT DOCUMENTS

| | | |
|---|---|---|
| 375102 | 6/1970 | European Pat. Off. . |
| 006638 | 1/1980 | European Pat. Off. . |
| 168526 | 1/1984 | European Pat. Off. . |
| 117553 | 9/1984 | European Pat. Off. . |
| 130064 | 1/1985 | European Pat. Off. . |
| 167309 | 1/1986 | European Pat. Off. . |
| 200032 | 11/1986 | European Pat. Off. . |
| 204284 | 12/1986 | European Pat. Off. . |
| 214761 | 3/1987 | European Pat. Off. . |
| 218272 | 4/1987 | European Pat. Off. . |
| 258068 | 3/1988 | European Pat. Off. . |
| 0304332 | 2/1989 | European Pat. Off. . |
| 305216 | 3/1989 | European Pat. Off. . |
| 330641 | 8/1989 | European Pat. Off. . |
| 331376 | 9/1989 | European Pat. Off. . |
| 334462 | 9/1989 | European Pat. Off. . |
| 341947 | 11/1989 | European Pat. Off. . |
| 4384717 | 8/1990 | European Pat. Off. . |
| 385401 | 9/1990 | European Pat. Off. . |
| 468102 | 1/1992 | European Pat. Off. . |
| 1617188 | 2/1971 | Germany . |
| 1617190 | 2/1971 | Germany . |
| 1940488 | 2/1971 | Germany . |
| 2044161 | 4/1971 | Germany . |
| 1767568 | 7/1971 | Germany . |
| 2101803 | 7/1971 | Germany . |
| 2032768 | 1/1972 | Germany . |
| 2121397 | 11/1972 | Germany . |
| 1803099 | 2/1978 | Germany . |
| 2137042 | 3/1980 | Germany . |
| 2137043 | 5/1980 | Germany . |
| 1617232 | 2/1982 | Germany . |
| 2925427 | 12/1983 | Germany . |
| 2730481 | 10/1986 | Germany . |
| 61-1168698 | 7/1986 | Japan . |
| WO 9009440 | 8/1990 | WIPO . |
| WO 9010695 | 9/1990 | WIPO . |
| WO 9102792 | 3/1991 | WIPO . |
| WO 9116422 | 10/1991 | WIPO . |
| WO 9211347 | 7/1992 | WIPO . |

Primary Examiner—Jon P. Weber
Assistant Examiner—Deborah Ware
Attorney, Agent, or Firm—Ernest G. Szoke; Wayne C. Jaeschke; Henry E. Millson, Jr.

[57] ABSTRACT

Enzyme granules having an average particle size of from about 1 to about 2.2 mm are disclosed. The enzyme granules comprise an extruded particulate first enzyme component containing at least one enzyme and organic and/or inorganic carrier material and a second particulate enzyme component containing at least one particulate enzyme different from the one enzyme in the said first enzyme component, wherein the second particulate enzyme component is agglomerated onto the particulate first enzyme component, and wherein the average particle size of the particulate first enzyme component is in the range of from about 1.1 to about 3 times the average particle size of the second particulate enzyme component. Furthermore, a process for the preparation of the enzyme granules is disclosed.

20 Claims, No Drawings

MULTI-ENZYME GRANULES

BACKGROUND OF THE INVENTION

1. Field of the Invention

This invention relates to enzyme granules containing at least two different enzymes, to a process for their production and to the use of the granules in solid or liquid detergents and cleaning formulations.

2. Statement of Related Art

Enzymes, especially proteases, are widely used in detergents, washing aids and cleaning products. Normally, the enzymes are not used as concentrates, but rather in the form of mixtures with a diluent/carrier material. If enzyme preparations of this type are added to conventional detergents, a considerable reduction in enzyme activity can occur during storage, especially if bleaching-active compounds are present. Application of the enzymes to carrier salts and simultaneous granulation in accordance with DE-OS 16 17 190 or by adhesion using nonionic surfactants in accordance with DE-OS 16 17 118 or aqueous solutions of cellulose ethers in accordance with DE-OS 17 87 568 does not lead to a significant improvement in storage stability because the sensitive enzymes are generally situated on the surface of the carrier in mixtures of the type in question. Although the stability of the enzymes in storage can be significantly increased by coating the enzymes with or encapsulating them in the carrier material and converting them into the required particle form by extrusion, pressing and spheronizing, as described for example in DE-PS 16 17 232, in DE-OS 20 32 768 and in DE-ASS 21 37 042 and 21 37 043, corresponding enzyme preparations have poor solubility properties. The undissolved particles can become caught up in and thus soil the washing or pass into the wastewater without being used. Although the encapsulating compositions known from DE-OS 18 03 099, which consist of a mixture of solid acids or acidic salts and carbonates or bicarbonates and which disintegrate on addition of water, improve the solubility of the enzyme preparations, they are extremely sensitive to moisture and, accordingly, require additional protective measures. Another disadvantage of the above-mentioned preparation is that the enzymes can only be processed in the form of dry powders. The fermenter broths typically accumulating in the enzyme production process cannot be used in this form, but have to be freed from water beforehand.

EP 168 526 describes enzyme granules which contain water-swellable starch, zeolite and a water-soluble granulation aid. This document proposes a production process for such formulations which overcomes the problem mentioned above and which essentially comprises concentrating a fermenter solution freed from insoluble constituents, introducing the additives mentioned and granulating the resulting mixture. The process using the additive mixture proposed therein is advantageously carried out with fermentation solutions which have been concentrated to a relatively high dry matter content, for example of 55% by weight.

International patent application WO 92/11347 describes enzyme granules for use in granular detergents and cleaning compositions which contain 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. These additives enable the enzyme to be processed without significant losses of activity. In addition, the storage stability of the enzymes in the granules is also satisfactory.

As demonstrated by way of example by the documents cited above, a broad prior art exists in the field of the production of granular enzyme preparations, so that various possibilities for making up individual enzymes in particulate form are available to the expert. Unfortunately, the methods mentioned fail when two or more enzymes capable of reacting with one another are to be incorporated in the same granule. This problem arises in particular in connection with protease which, as a protein-degrading enzyme, is of course capable of decomposing a second enzyme and/or other enzyme present at the same time. If this decomposition process takes place during the production and/or storage of the enzyme granules, the effect of the second enzyme and/or other enzymes under in-use conditions is no longer guaranteed.

Solutions to this problem have also been proposed in the prior art. Thus, according to International patent application WO 90/09440, two-enzyme granules are produced by coating a protease- and cellulose-containing core with a total of 10 layers (alternately stearic acid/palmitic acid glyceride and kaolin) the quantity of protective coating material in the Examples exceeding the quantity of core, subsequently applying a mixture of a second enzyme, a binder, a filler and a granulation aid and, finally, applying an outer coating. A production process such as this is unfavorable on account of the large amount of separating material required between the enzyme-containing core and the layer containing the second enzyme which lies further to the outside.

It is known from European patent application EP 304 332 that enzyme-containing basic granules can be coated with powder-form components containing a second enzyme. However, this method of producing multi-enzyme granules leads to inadequate stability of the second enzyme present in the outer layer which, in addition, has to be prepared beforehand in powder form—another disadvantage of this method.

DESCRIPTION OF THE INVENTION

Accordingly, the problem addressed by the present invention was to provide a simple process for producing particulate enzyme preparations containing at least two different enzymes reacting with one another which would enable the enzymes to be incorporated in the multi-enzyme granules without any loss of activity and to remain therein in storage-stable manner. Surprisingly, this problem has essentially been solved by the use of two separately produced granules with different particle sizes each containing an enzyme in a subsequent co-granulation step in which the smaller granules agglomeratingly encapsulate the larger granules.

Accordingly, the present invention relates to a process for the production of enzyme granules with average particle sizes of 1 mm to 2.2 mm which contain at least two different enzymes by extruding an enzyme compound formed by mixing a fermentation broth of a first enzyme—optionally freed from insoluble constituents and concentrated—with organic and/or inorganic carrier material and optionally granulation aids as additives, optionally spheronizing the extrudate in a spheronizer, drying, mixing with a particulate second enzyme and optionally other particulate enzymes under agglomeration conditions, a binder optionally being used, and optionally applying a dye- or pigment-containing coating, the average particle size of the extrudate core containing the first enzyme being 1.1 to 3 times, preferably 1.1 to 2.5 times and, more preferably, 1.3 to 2 times the average particle size of the second particulate enzyme or further particulate enzymes. By virtue of these size ratios, the contact areas between the particles to be agglomerated, based on the surface as a whole, are particularly favorable.

The present invention also relates to enzyme granules suitable for incorporation in detergents or cleaning compositions, more especially particulate detergents or cleaning compositions, and containing enzyme and inorganic and/or organic carrier material and optionally granulation aids, characterized in that they consist of an extruded core containing a first enzyme onto which particles containing a second enzyme and optionally particles containing further enzymes are agglomerated and of an outer coating applied by spraying, the average particle size of the particles containing a second enzyme or the other enzymes separately prepared beforehand being 0.5 to 0.9 times the average particle size of the extrudate core.

The enzyme in the core of the granules is preferably protease while the enzyme or—where several various smaller particles are used—the enzymes present in the smaller separately produced particles which agglomerate onto the extrudate are amylase, lipase, cellulase and/or oxidase, although the process according to the invention is also successful when the protease is present in the smaller particles to be agglomerated on and one of the other enzymes mentioned is present in the extrudate core.

In another preferred embodiment, the enzyme granules according to the invention contain protease in their extruded core and lipase in the smaller particles agglomerated thereon, the lipase preferably being obtainable from Humicola lanuginosa as described, for example, in European patent applications EP 258 068, EP 305 216 and EP 341 947, from bacillus species as described, for example, in International patent application WO 91/16422 or European patent application EP 384 717, from pseudomonas species as described, for example, in European patent applications EP 468 102, EP 385 401, EP 375 102, EP 334 462, EP 331 376, EP 330 641, EP 214 761, EP 218 272 or EP 204 284 or International patent application WO 90/10695, from fusarium species as described, for example, in European patent application EP 130 064, from rhizopus species as described, for example, in European patent application EP 117 553 or from aspergillus species as described, for example, in European patent application EP 167 309. Suitable lipases are commercially obtainable, for example, under the names of Lipolase®, Lipozym®, Amano®-Lipase, Toyo-Jozo®-Lipase, Meito®-Lipase and Diozynth®-Lipase.

Multi-enzyme granules according to the invention which contain protease in their extrudate core and amylase in the smaller particles to be agglomerated on are particularly suitable for use in dishwashing detergents, particularly machine dishwashing detergents. The opposite composition, i.e. amylase in the extrudate core and protease in the smaller particles, is also possible. Suitable amylases are commercially obtainable, for example, under the names of Maxamyl® and Termamyl®.

In another preferred embodiment of the invention, the enzyme granules according to the invention contain two different types of smaller particles agglomerated onto a protease-containing extrudate core, the smaller particles containing either lipase or cellulase. Corresponding enzyme granules according to the invention can be produced by successively agglomerating on first one and then the other smaller enzyme particle. However, by virtue of its simplicity, the preferred procedure is to mix the two smaller enzyme particles with the extrudate core and simultaneously to agglomerate both the smaller enzyme particles onto the extrudate core.

Suitable enzymes for the extrudate core (first enzyme) of the enzyme granules according to the invention are above all the proteases, lipases, amylases, cellulases and oxidases obtained from microorganisms, such as bacteria or fungi, proteases, especially those produced from bacillus species, being preferred. They may be obtained in known manner by fermentation processes from suitable microorganisms which are described, for example, in DE-OSS 19 40 488, 20 44 161, 22 01 803 and 21 21 397, from U.S. Pat. Nos. 3,632,957 and 4,264,738, in European patent application EP 006 638 and in International patent application WO 91/2792.

The first enzyme is preferably present in the granules according to the invention in quantities of 4% by weight to 20% by weight. If the enzyme granules according to the invention are a protease-containing formulation, the protease activity is preferably 70,000 protease units (PU, as determined by the method described in Tenside 7 (1970) 125) to 350,000 PU and, more preferably, 120,000 PU to 300,000 PU per gram of enzyme granules.

The production of the particles containing the first enzyme, the so-called extrudate cores, onto which the smaller particles containing the second enzyme agglomerate, comprises an extrusion step as described below.

The production of the smaller particles containing the second enzyme is not confined to one particular process, although it is important to ensure that the production process gives enzyme granules with the average particle sizes required for the process according to the invention. Accordingly, it is also possible to produce the smaller particles containing the second enzyme by the extrusion process described, for example, in International patent application WO 92/11347 or European patent EP 168 526. The particles containing the second enzyme are preferably produced by pan granulation from an inorganic and/or organic carrier material and an aqueous enzyme solution. A corresponding process using inorganic salt and cellulose fibers in the carrier material and water and/or a wax-like substance as binder is described, for example, in German patent DE 27 30 481. The other constituents of the smaller particles present in addition to the second enzyme are not critical either although typical ingredients of detergents or at least substances compatible therewith are preferred for the preferred use of the enzyme granules according to the invention in detergents. The smaller particles containing the second enzyme preferably contain inorganic salt, more particularly alkali metal sulfate and/or chloride, in quantities of—based on the smaller particles as a whole—30% by weight to 80% by weight, fibrous or powder-form cellulose in quantities of 2% by weight to 40% by weight, binders, more particularly dextrose, sucrose, polyvinyl alcohol and/or polyvinyl pyrrolidone, in quantities of 0.1% by weight to 15% by weight.

In principle, suitable carrier materials for the first enzyme present in the extrudate core are any organic or inorganic powder-form substances which destroy or deactivate the enzymes to be granulated to only a negligible extent, if at all, and which are stable under extrusion and the subsequent granulation conditions. Substances such as these include, for example, starch, cereal flour, cellulose powder, alkali metal alumosilicate, more particularly zeolite, layer silicate, for example bentonite or smectite, and water-soluble inorganic or organic salts, for example alkali metal chloride, alkali metal sulfate, alkali metal carbonate or alkali metal acetate, sodium or potassium being the preferred alkali metals. A carrier mixture of water-swellable starch, cereal flour and optionally cellulose powder and also alkali metal carbonate is preferably used.

The water-swellable starch is preferably corn starch, rice starch, potato starch or mixtures thereof, corn starch being particularly preferred. Swellable starch is present in the extrudate cores preferably in quantities of 20% by weight to 50% by weight and more preferably in quantities of 25% by weight to 45% by weight, based on the extrudate core. The sum total of the quantities of swellable starch and flour is preferably not more than 80% by weight and, more preferably, is between 32% by weight and 65% by weight.

The cereal flour is a product obtainable in particular from wheat, rye, barley or oats or a mixture of such flours, whole-grain flours being preferred. A whole-grain flour is understood to be a flour which has not been fully ground and which has been produced from or consists at least predominantly of whole unshelled grains, the rest consisting of fully ground flour or starch. Commercial wheat flours, such as Type 440 to Type 550, are preferably used. Ground products of the cereal leading to the swellable starches mentioned above may also be used providing it is ensured that the flours have been produced from whole grains. It is known that the flour component of the additive mixture provides for a significant reduction in the odor of the enzyme preparation which exceeds by far the reduction in odor produced by the incorporation of equal quantities of corresponding starch types. Corresponding cereal flour is present in the enzyme granules according to the invention in quantities of, preferably, 10% by weight to 35% by weight and, more preferably, 15% by weight to 25% by weight.

Granulation aids may be present as additional constituents of the carrier material for the first enzyme present in the extrudate core, including for example cellulose or starch ethers, such as carboxymethyl cellulose, carboxymethyl starch, methyl cellulose, hydroxyethyl cellulose, hydroxypropyl cellulose and corresponding cellulose mixed ethers, gelatine, casein, tragacanth, maltodextrose, sucrose, invert sugar, glucose sirup or other water-soluble or readily water-dispersible oligomers or polymers of natural or synthetic origin. Synthetic water-soluble polymers include alkyl and alkenyl polyethoxylates, polyethylene glycols, polyacrylates, polymethacrylates, copolymers of acrylic acid with maleic acid or compounds containing vinyl groups, also polyvinyl alcohol, partly hydrolyzed polyvinyl acetate and polyvinyl pyrrolidone. Where the granulation aids mentioned above contain carboxyl groups, they are normally present in the form of their alkali metal salts, more particularly their sodium salts. Corresponding granulation aids may be present in the enzyme extrudates according to the invention in quantities of up to 10% by weight and, more particularly, in quantities of 0.5% by weight to 8% by weight, based on the extrudate core. Polyethylene glycols are preferably selected from those having average molecular weights of 200 to 600. Although polyethylene glycols of higher molecular weight, i.e. those with an average molecular weight above 1,000, may be used as synthetic water-soluble polymers with a good dust-binding effect, the relatively high molecular weight polyethylene glycols can often produce an unwanted increase in the dissolving time of the extrudate core under in-use conditions so that these substances are preferably missing from the extrudate core of the enzyme granules according to the invention. The degree of substitution in carboxymethyl celluloses preferably used is in the range from 0.8 to 0.95 because particularly strong granules are obtained where corresponding carboxymethyl celluloses are used or smaller quantities are required to obtain granules of a certain strength than where cellulose having a relatively low degree of substitution is used. In addition, by using the above-mentioned carboxymethyl cellulose with a relatively high degree of substitution, a higher throughput through the extruder can be achieved in the extrusion step of the granule production process. The degree of substitution of the carboxymethyl cellulose is understood to be the number of etherified oxygen atoms bearing a carboxymethyl group per saccharide monomer of the cellulose.

In one preferred embodiment, the extrudate core of the enzyme granules according to the invention contains 4% by weight to 20% by weight, expressed as dry matter, of protease, lipase, amylase and/or cellulase, 70% by weight to 90% by weight of inorganic and/or organic carrier material and 5% by weight to 50% by weight of carboxymethyl-cellulose-containing granulation aid, balance to 100% by weight water.

The extrudate core of the enzyme granules according to the invention preferably contains as granulation aid a mixture of—based on the extrudate core—0.1% by weight to 10% by weight and, more particularly, 0.5% by weight to 5% by weight of carboxymethyl cellulose and 0.1% by weight to 10% by weight and, more particularly, 0.5% by weight to 4% by weight of polyethylene glycol with an average molecular weight of 200 to 600 and/or of an alkyl or alkenyl polyethoxylate corresponding to formula (I):

$$R-(OCH_2CH_2)_n-OH \qquad (I)$$

in which R is a linear or branched alkyl or alkenyl radical containing up to 3 C—C double bonds and 10 to 22 and, more particularly, 12 to 18 carbon atoms and n (average degree of ethoxylation) is a number of 30 to 80.

The enzyme granules according to the invention are preferably produced from fermenter broths which are freed from insoluble impurities, for example by microfiltration. The microfiltration is preferably carried out as crossflow microfiltration using porous tubes with micropores larger than 0.1 μm in size, flow rates of the concentrate solution of more than 2 m/s and a pressure difference to the permeate side of less than 5 bar, as described for example in European patent application EP 200 032. The microfiltration permeate is then concentrated, preferably by ultrafiltration optionally followed by vacuum evaporation. The concentration process may be carried out as described in International patent application WO 92/11347 in such a way that only relatively low dry matter contents of, preferably, 5% by weight to 50% by weight and, more preferably, 10% by weight to 40% by weight are obtained. The concentrate is added to a dry, powder-form or granular mixture of the above-described additives best prepared in advance. The additives are preferably selected from the carrier materials and granulation aids mentioned in such a way that the enzyme extrudate formed has an apparent density of 700 g/l to 1200 g/l. The water content of the mixture should be selected so that it can be converted during compounding with stirring and beating tools into granular particles non-tacky at room temperature and can be plastically deformed and extruded under relatively high pressures. The free-flowing compound is then processed in basically known manner in a kneader and an adjoining extruder to form a plastic, substantially homogeneous paste which can undergo an increase in temperature to between 40° and 60° C. and, more particularly, to between 45° and 55° C. as a result of compounding. The material leaving the extruder is passed through a multiple bore die followed by a cutting blade so that it is reduced to cylindrical particles of predetermined size. The diameter of the bores in the multiple-bore die is best from 0.7 mm to 1.2 mm and preferably from 0.8 mm to 1.0 mm. The length-to-thickness ratio of the extrudate is preferably in the range from 0.9 to 1.1:1 and, more preferably, is 1.0:1. The particles present in this form may then be directly further processed, optionally after a drying step. However, it has been found to be of advantage to spheronize the cylindrical particles leaving the extruder and cutter, i.e. to round them off and to "deflash" them in suitable machines. A corresponding spheronizing process is described, for example, in DE-ASS 21 37 042 and 21 37 043. It is carried out in a machine consisting of a cylindrical container with stationary, fixed side walls and a friction plate rotatably mounted on its base. Machines of this type are marketed under the name of Marumerizer®. After spheronizing, the still moist spherical particles are dried continuously or in batches, preferably in a fluidized bed dryer, at feed air temperatures of preferably 35° C. to 50° C. and, more particularly, at a maximum product temperature of 45° C. to a residual moisture content of 4% by weight to 10% by weight and preferably 5% by weight to 8% by weight if they previously had higher water contents. At this stage of the process, any dust-like fractions smaller than 0.1 mm and, more particularly, 0.4 mm in size occurring during the production of the extrudate core and any coarse fractions larger than 2 mm and, more particularly, 1.6 mm in size can be removed by sieving or air separation and optionally returned to the production process. The extrusion process is preferably carried out in such a way that the extrudate cores formed, which are suitable for the enzyme granules according to the invention, have such a particle size distribution that less than 10% by weight and, more particularly, less than 2% by weight of the particles are smaller than 0.2 mm in diameter, 10% by weight to 20% by weight of the particles are 0.2 mm to less than 0.4 mm in diameter and 80% by weight to 90% by weight of the particles are from 0.4 mm to less than 0.8 mm in diameter.

Substances for encapsulating and coating the extrudate particles may be additionally introduced after or preferably during the drying process. This can be of particular advantage when the correspondingly produced extrudate core suitable for the purposes of the invention is to be intermediately stored for a prolonged period pending its subsequent processing to the enzyme granules according to the invention. If the other processing steps are directly carried out, there is generally no need to apply a protective coating to the extrudate core.

The core particle thus obtained, which contains the first enzyme, is mixed with a second enzyme made up into particles in any way and, optionally, other particulate enzymes under agglomeration conditions, the particles to be mixed with the extrudate having to have such a mean particle diameter that the average particle size of the extrudate containing the first enzyme is 1.1 to 3 times the average particle size of the second particulate enzyme or other particulate enzymes. The smaller particles containing the second enzyme or the other enzymes preferably have such a size distribution that less than 25% and, more particularly, less than 20% of the particles have a diameter of less than 0.5 mm, 20% to 60% of the particles have a diameter of 0.5 mm to 0.87 mm and 100% of the particles have a diameter below 1.2 mm. By contrast, preferably less than 10% and, more preferably, less than 6% of the extrudate cores have a diameter below 0.61 mm while less than 10% of the extrudate cores have a diameter above 1.23 mm and, more particularly, above 1.22 mm.

The quantity ratios between the extrudate core and the smaller enzyme particle are preferably selected in dependence upon the various particle sizes. Thus, in the case of extrudate cores with an average particle diameter 2.5 to 3 times that of the smaller enzyme particles, it is possible in accordance with the invention to adjust the ratio by weight of extrudate core to smaller enzyme particle to a value of 30:70 to 90:10 and, more particularly, to a value of 40:60 to 60:40. If the extrudate cores have an average particle diameter 1.8 to 2.2 times that of the smaller enzyme particles, corresponding ratios by weight of at least 70:30 are preferred.

The pan granulation process is preferably carried out by spraying the mixture of enzyme-containing particles in a fluidized bed with a typical binder which, in its most simple form, may be water. Other suitable binders are nonionic surfactants and, more particularly, film formers selected from the water-soluble organic polymers mentioned above, for example carboxymethyl cellulose and/or polyethylene glycol, which may be used as such or, more particularly, in the form of aqueous solutions. Suitable nonionic surfactants are in particular those which are solid at room temperature and just sufficiently liquid at the agglomeration temperature to be capable of binding the extrudate cores to the smaller enzyme particles. In addition, dyes or pigments may also be applied to the particles at the agglomeration stage in order to mask or modify any coloration present in the particles which generally emanates from the enzyme concentrate. Titanium dioxide and calcium carbonate have proved to be particularly suitable inert and physiologically safe pigments, being introduced subsequently or preferably together with the binder in the form of an aqueous dispersion. The water introduced with the pigment dispersion or with the binder is removed again during the drying step which is carried out at the same time or which may have to be carried out at a later stage.

In the process step where the individual enzyme-containing particles are joined together to form the enzyme granules according to the invention, an aqueous dispersion containing 40% to 75% by weight of water, 15% by weight to 30% by weight of film-forming polymer, more particularly a mixture of polyethylene glycol with an average molecular weight of 8,000 to 15,000 and carboxy-methyl cellulose in a ratio by weight of 30:1 to 50:1, and 5% by weight to 30% by weight of pigment, more particularly a mixture of titanium dioxide and calcium carbonate in a ratio by weight of 5:1 to 10:1, is preferably sprayed onto the enzyme-containing particles as binder. The quantity of binder introduced is preferably no more than 40% by weight and, more particularly, from 10% by weight to 35% by weight, based on the enzyme-containing particles as a whole. Where water or a water-containing binder in particular is used, drying is carried out in a following step or preferably during application of the aqueous binder to water contents, based on the enzyme granules formed, of 5% by weight to 10% by weight and, more particularly, 7% by weight to 9% by weight.

In another embodiment of the process according to the invention, only part rather than all the larger extrudate cores are coated with the smaller enzyme particles providing this leads to adequate activities of second enzyme for the required application of the resulting mixture of enzyme granules according to the invention and extrudate core uncoated with second enzyme.

The enzyme granules according to the invention are preferably used for the production of solid and, more particularly, particulate detergents or cleaning formulations which may be obtained by simple mixing of the enzyme granules with other powder components typically present in such formulations. A preferred application, more particularly for protease/amylase granules according to the invention, is in the field of machine dishwashing detergents which are preferably formulated as compacted powders with high apparent densities preferably in the range from 750 to 1000 g/l or in tablet form. To produce tablets, the enzyme granules according to the invention are preferably mixed with all other components in a mixer and the resulting mixture is tabletted in conventional tablet presses, for example eccentric or rotary presses, under pressures in the range from $200 \cdot 10^5$ Pa to $1500 \cdot 10^5$ Pa. Breaking-resistant tablets which still dissolve sufficiently quickly under in-use conditions are readily obtained in this way, typically with flexural strengths in excess of 150N. A correspondingly produced tablet preferably has a weight of 15 g to 40 g and, more particularly, 20 g to 30 g for a diameter of 35 mm to 40 mm.

For incorporation in particulate detergents and cleaning formulations, the enzyme granules preferably have average particle sizes of 0.9 mm to 1.8 mm and, more preferably, in the range from 1.0 mm to 1.5 mm. The granules according to the invention preferably contain less than 5% by weight and, more preferably, at most 1% by weight of particles with sizes outside the 0.2 mm to 1.6 mm range.

The enzyme preparation obtained in accordance with the invention consists of substantially rounded, dust-free particles which generally have an apparent density of around 650 to 1050 grams per liter and, more particularly, 700 to 880 grams per liter. The apparent densities mentioned generally correspond to those of the starting particles. The granules according to the invention are distinguished by very high stability in storage, more particularly at temperatures above room temperature and at high atmospheric humidity levels, which—although enzymes capable of reacting with one another are present—does not exceed the stability in storage of the separately stored components extrudate core and smaller enzyme particle. This applies both to the enzyme granules according to the invention or their components as such and to the enzyme granules according to the invention or their components incorporated in particulate detergents or cleaning formulations. Another advantage of the enzyme granules according to the invention is their rapid dissolvability in the wash liquid under in-use conditions. In water at 25° C., the granules according to the invention preferably release 100% of their enzyme activity within 3 minutes and, more particularly, within 70 seconds to 2 minutes.

EXAMPLES

Example 1

A biomass-containing fermenter broth containing around 65,000 protease units per gram (PU/g) was obtained by fermentation of Bacillus licheniformis (ATCC 53926)—modified by the process described in International patent application WO 91/2792 by transformation of a gene sequence from Bacillus lentus DSM 5483—using the process described in German patent DE 27 25 427. The fermenter broth was concentrated to a protease content of 700,000 PU/g by decantation, crossflow microfiltration, ultrafiltration (cutoff limit at molecular weight 10,000) and subsequent concentration by evaporation in vacuo by the process described in International patent application WO 92/11347. The fermenter broth thus concentrated was mixed with the additives listed in Table 1 in a mixer equipped with a rotating beating tool and the resulting mixture was homogenized in an externally cooled kneader. The plastic material was extruded in an extruder equipped with a multiple-bore extrusion die (bore diameter 0.9 mm) and a rotating blade. The 0.9 mm long extrudate cores X1 to X4 characterized by their composition in Table 1 were obtained and were then treated and "deflashed" in a spheronizing machine (Marumerizer®) for about 1 minute to form uniformly rounded particles. The material leaving the spheronizer was dried in a fluidized bed dryer for 15 minutes at temperatures of 40° to 45° C. to a water content of 6% by weight. Particles smaller than 0.4 mm and larger than 1.6 mm in size (quantity: 1.2% by weight) were removed by subsequent sieving and returned to the process at the additive mixing stage.

TABLE 1:

Composition of the extrudates [% by weight]

|  | X1 | X2 | X3 | X4 |
|---|---|---|---|---|
| Fermenter broth | 34 | 32 | 32 | 32 |
| Cellulose powder[a] | 4.5 | 4.5 | 4.5 | 4.5 |
| Sucrose | 3.5 | 3.5 | 3.5 | 3.5 |
| Wheat flour T 450 | 19 | 19 | 19 | 19 |
| Corn starch | 37 | 38 | 39 | 36 |
| CMC-I[b] | 2 | 2 | — | 3 |
| CMC-II[c] | — | — | 1 | — |
| PEG[d] | — | 1 | — | 2 |
| Surfactant[e] | — | — | 1 | — |

[a] Technocel® 30 (a product of Cellulose Fullstoff Fabrik)
[b] Carbocel® 300 (degree of substitution 0.65–0.75; a product of Lamberti CMC)
[c] Carbocel® 500 (degree of substitution 0.85–0.95; a product of Lamberti CMC)
[d] Polyethylene glycol, average molecular weight 400
[e] 40x Ethoxylated tallow fatty alcohol (a product of Henkel KGaA)

The extrudate cores X1, X2, X3 and X4 (average particle size 918 µm) were mixed with lipase granules (Lipolase®, a product of Novo, average particle size 668.5 µm, lipase activity 100,000 LU/g) in a ratio by weight of 3.3:1. The protease/lipase mixture was coated in the fluidized bed of an Aeromatic STREA-1 fluidized bed spray granulator. The coating suspension consisted of:

| Titanium dioxide | 17% |
| Carboxymethyl cellulose | 0.5% |
| Calcium carbonate | 2.5% |
| Polyethylene glycol, average molecular weight 12,000 | 19% |
| Water | 61% |

During application of the aqueous coating suspension by spraying, the finer lipase granules agglomerated onto the coarse protease extrudates. During coating, the following operating parameters were established for simultaneous drying:

| Product temperature: | 36° C. |
| Feed air temperature: | 47° C. |
| Waste air temperature: | 33° C. |

After 28.8% by weight, based on the enzyme mixture initially introduced, of the above-mentioned coating suspension had been sprayed on, the granules were uniformly encapsulated in the coloring and protective layer. At the same time, the lipase particles had been combined with the protease granules and were uniformly distributed in the end product of the enzyme mixture. The solubility of the enzyme mixture was 1 minute and 26 seconds. The storage stability tests did not reveal any changes in relation to storage tests on separately stored lipase and protease granules. There was also no discernible increase in dust abrasion.

Example 2

As described in Example 1, extrudate cores X1, X2, X3 and X4 were mixed with amylase granules (Maxamyl® CXT 5000, a product of Gist Brocades, average particle size 306 μm) in a ratio by weight of 1.1:1 and coated. The coating suspension consisted of

| | |
|---|---|
| Titanium dioxide | 17% |
| Stearyl alcohol | 19% |
| Eumulgin ® RT 40<sup>a)</sup> | 3% |
| Water | 61% |

<sup>a)</sup>40x Ethoxylated castor oil (a product of Henkel KGaA)

During spray application of the aqueous coating suspension, the water only evaporated completely after impinging on the granules. As long as the coating suspension on the granules remained flowable, the fine amylase granules adhered to the surface of the coarser protease granules. After evaporation of the water from the coating suspension, the coating layer formed a firm bond between the various enzyme granules. In addition, the enzyme agglomerate was coated with the protective coating layer.

The amylase granules were uniformly distributed in the enzyme mixture. There was no difference in storage stability, solubility and dust abrasion in relation to products consisting of only one type of enzyme.

Example 3

The procedure was as in Example 2. In this case, the amylase granules adhered to the protease granules through the spray application of a nonionic surfactant with a low pour point. A $C_{16-18}$ fatty alcohol 5EO (Dehydol® TA5, a product of Henkel KGaA) was used as the nonionic surfactant. The pour point of the surfactant was around 35° C. The product temperature in the fluidized bed was 35° to 39° C. At these temperatures, the nonionic surfactant was still flowable and was uniformly distributed over all the enzyme granules. Since spraying was carried out in the vicinity of the pour point of the nonionic surfactant, the surfactant was already viscous and the amylase remained "sticking" to the individual protease granules. 50 g of nonionic surfactant were sprayed on per kg of enzyme particles.

The agglomerates were then encapsulated in a coating melt applied by spraying and were thus protected and colored uniformly white.

11.4% of the coating melt was used for 1 kg of the enzyme granules. The coating shell had the following composition, based on the end product formed:

| | |
|---|---|
| Stearyl alcohol | 5.4% |
| Eumulgin ® RT 40 | 1.3% |
| Titanium dioxide | 4.7% |

Example 4

Retaining the other process parameters of Example 3, a melt (temperature around 40° C.) of 67% by weight of technical stearyl alcohol, 10% by weight of 40×ethoxylated fatty alcohol (Disponil® TA 430, a product of Henkel KGaA) and 23% by weight of titanium dioxide was sprayed onto a mixture (ratio by weight 2:1:1) of protease extrudate X1, lipase granules (Lipolase® as in Example 1) and cellulase granules (Celluzyme® 0.7 T, a product of Novo Nordisk; average particle size around 500 μm). The smaller lipase and cellulase granules agglomerated onto the protease extrudate and the three-enzyme granules formed were encapsulated in the melt applied by spraying and were thus protected and colored uniformly white. 21.5% of the coating melt were used, based on the multi-enzyme granules formed.

We claim:

1. A process for the production of enzyme granules having an average particle size of from about 1 to about 2.2 mm and which contain at least two different enzymes comprising the steps of
    A) extruding a first particulate enzyme composition formed by mixing at least one fermentation broth of an enzyme with organic and/or inorganic carrier material;
    B) optionally spheronizing the extruded first particulate enzyme composition,
    C) drying the extruded first particulate enzyme composition as needed to a residual moisture content in the range of from about 4% to about 10% by weight;
    D) forming a second particulate enzyme composition comprised of at least one particulate enzyme different from the enzyme in said first particulate enzyme composition, wherein fewer than about 25% of the particles in the second particulate enzyme composition are smaller than about 0.5 mm in diameter;
    E) mixing the second particulate enzyme composition with the extruded first particulate enzyme composition and a binder to agglomerate the second particulate enzyme composition onto the extruded first particulate enzyme composition to produce said enzyme granules;
wherein the average particle size of the extruded first particulate enzyme composition is in the range of from about 1.1 to about 3 times the average particle size of the second particulate enzyme composition.

2. The process of claim 1 wherein in step A) the at least one fermentation broth is first freed from insoluble constituents and then concentrated.

3. The process of claim 1 wherein in step A) a granulation aid is also present.

4. The process of claim 1 wherein the average particle size of the extruded first particulate enzyme composition is in the range of from about 1.1 to about 2.5 times the average particle size of the second particulate enzyme composition.

5. The process of claim 4 wherein the average particle size of the extruded first particulate enzyme composition is in the range of from about 1.3 to about 2 times the average particle size of the second particulate enzyme composition.

6. The process of claim 1 wherein the first particulate enzyme composition contains a protease and the second particulate enzyme composition contains at least one particulate enzyme selected from the group consisting of lipase, amylase, cellulase, and oxidase.

7. The process of claim 1 wherein the first particulate enzyme composition contains a lipase and the second particulate enzyme composition contains at least one particulate enzyme selected from the group consisting of protease, amylase, cellulase, and oxidase.

8. The process of claim 1 wherein step E) is carried out by spraying the mixture with a binder comprising from about 40 to about 75% by weight of water, from about 15 to about 30% by weight of a film-forming polymer, and from about 5 to about 30% by weight of a pigment.

9. The process of claim 8 wherein the quantity of binder is from about 10 to about 40% by weight, based on the weight of the sum of the first and second enzyme compositions.

10. The process of claim 8 wherein following step E) the resulting mixture is dried to a water content of from about 5 to about 10% by weight.

11. The process of claim 8 wherein the film-forming polymer is a mixture of (a) polyethylene glycol having an average molecular weight of from about 8,000 to about 15,000 and (b) carboxymethyl cellulose in a ratio by weight of (a) to (b) of about 30:1 to about 50:1.

12. The process of claim 11 wherein the pigment is a mixture of (a) titanium dioxide and (b) calcium carbonate in a ratio by weight of (a) to (b) of from about 5:1 to about 10:1.

13. Enzyme granules having an average particle size of from about 1 to about 2.2 mm which comprise an extruded first particulate enzyme composition containing at least one enzyme and organic and/or inorganic carrier material and a second particulate enzyme composition containing at least one particulate enzyme different from the at least one enzyme in said first particulate enzyme composition, wherein the second particulate enzyme composition is agglomerated onto the extruded first particulate enzyme composition, and wherein the average particle size of the extruded first particulate enzyme composition is in the range of from about 1.1 to about 3 times the average particle size of the second particulate enzyme composition.

14. The enzyme granules of claim 13 wherein in the second particulate enzyme composition less than 25% of the particles are smaller than 0.5 mm in diameter.

15. The enzyme granules of claim 13 wherein the granules are provided with an outer coating.

16. The enzyme granules of claim 13 wherein the first particulate enzyme composition contains a protease and the second particulate enzyme composition contains a lipase.

17. The enzyme granules of claim 13 wherein the first particulate enzyme composition contains a lipase and the second particulate enzyme composition contains a protease.

18. The enzyme granules of claim 13 wherein the first particulate enzyme composition contains from about 20 to about 50% by weight of a water-swellable starch.

19. The enzyme granules of claim 13 wherein the first particulate enzyme composition comprises from about 4 to about 20% by weight of enzyme, from about 70 to about 90% by weight of carrier material, and from about 5 to about 50% by weight of a granulation aid, the above percentages being based on dry weight.

20. The enzyme granules of claim 13 wherein the particles of the first particulate enzyme composition have a length-to-thickness ratio of from about (0.9–1.1):1.

* * * * *